United States Patent [19]

Gray et al.

[11] 4,168,281
[45] Sep. 18, 1979

[54] CYCLOPENTANE ALDEHYDES

[75] Inventors: Robin T. Gray; Aaldert J. De Jong, both of Amsterdam, Netherlands

[73] Assignee: Shell Oil Company, Houston, Tex.

[21] Appl. No.: 864,561

[22] Filed: Dec. 27, 1977

[51] Int. Cl.² ............................................. C07C 47/30
[52] U.S. Cl. ...................................... 260/598; 252/522
[58] Field of Search ........................................ 260/598

[56] References Cited

U.S. PATENT DOCUMENTS

| | | | |
|---|---|---|---|
| 2,584,539 | 2/1952 | Bordenca et al. | 260/598 |
| 2,815,378 | 12/1957 | Klein | 260/598 X |

OTHER PUBLICATIONS

Chemical Abstract, Index Guide (1977) 924G.
Strickler et al. (II), Tetrahedron Letters, No. 12 (1964) 649–655.
Strickler et al., Helvetica Chimica Acta, vol. 50 (3) (1967) 759–767.
Strickler et al., Chem. Abs., vol. 67 (1967) 3147x.

*Primary Examiner*—Bernard Helfin

[57] ABSTRACT

Novel cyclopentane derivatives of the formula:

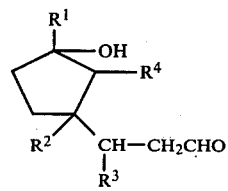

wherein $R^1$ and $R^4$ each represents an alkyl group and $R^2$ and $R^3$ each represents a hydrogen atom or alkyl group, are useful as aroma chemicals.

3 Claims, No Drawings

CYCLOPENTANE ALDEHYDES

BACKGROUND OF THE INVENTION

This invention relates to a novel class of cyclopentane derivatives ring substituted with carboxyaldehyde and hydroxy functional groups which are of interest as aroma chemicals.

A variety of hydroxy- and carbonyl-substituted organic compounds are known in the art to possess aroma properties which are useful in the perfumery field. These compounds, which can be of natural or synthetic origin, include hydroxy-aldehydes, esters, aldehydes, ketones and alcohols, having a board spectrum of perfume-like odors. While, as noted, the aromas from known compounds or combinations of compounds can be quite varied, there still exists a continuing need for new compounds which accent particular fragrances or other odorant properties, especially when such compounds can be obtained by relatively simple and economic processing techniques.

SUMMARY OF THE INVENTION

A novel class of cyclopentane derivatives ring substituted with aliphatic carboxyaldehyde and hydroxy moieties have now been found which possess distinctive floral odors. This novel class of cyclopentane derivatives is represented by the general formula (I):

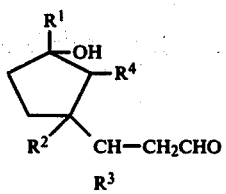

I wherein $R^1$ and $R^4$ each represents an alkyl group; and $R^2$ and $R^3$ each represents a hydrogen atom or an alkyl group.

DESCRIPTION OF THE PREFERRED EMBODIMENTS

Preferred cyclopentane derivatives of formula (I) above are those in which $R^1$ and $R^4$ each is an alkyl group of 1 to 4 carbon atoms with one of $R^2$ and $R^3$ being an alkyl group of 1 to 4 carbon atoms and the other of $R^2$ and $R^3$ being hydrogen. Most preferably, $R^1$ and $R^4$ each represents methyl and $R^2$ and $R^3$ each represents hydrogen or methyl provided that when one of the groups $R^2$ and $R^3$ is methyl the other is hydrogen. In this regard, the cyclopentane derivatives of the instant invention are structurally related to the aliphatic carboxyaldehyde- and hydroxy- or epoxy-substituted cyclohexanes described in our copending U.S. Patent application Ser. No. 818,262 filed July 22, 1977 and now U.S. Pat. No. 4,122,121.

Examples of the preferred compounds according to formula (I) above are:
3-(2,3-dimethyl-3-hydroxycyclopentyl)butanal
3-(1,2,3-trimethyl-3-hydroxycyclopentyl)propanal.

In this regard, 3-(2,3-dimethyl-3-hydroxy-cyclopentyl)butanal is particularly preferred in view of its exceptional floral odor and ease of preparation.

The compounds of the invention may be prepared by a process which comprises hydroformylating an olefin of formula (II):

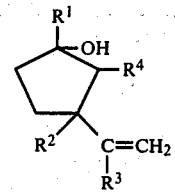

II in which the symbols $R^1$, $R^2$, $R^3$ and $R^4$ have the meanings given for formula (I) above, in the presence of a metal carbonyl catalyst. The catalyst may be a cobalt or rhodium carbonyl catalyst but is preferably a rhodium carbonyl complex, in particular a complex which also contains hydride and/or phosphine groups. The catalyst may be a homogeneous catalyst such as the compound $RhH(CO)[P(C_6H_5)_3]_3$ or a heterogeneous catalyst such as that obtained by incorporating the above mentioned rhodium carbonyl complex onto a solid carrier such as silica. The temperature of the hydroformylation reaction is preferably from 50° C. to 200° C. and the total pressure of the carbon monoxide and hydrogen used is preferably up to 200 atm. The process may be carried out in an organic solvent, for example, an aliphatic, cycloaliphatic or aromatic hydrocarbon.

The olefinic starting materials of formula II which are useful in preparing the compounds of the invention may be obtained from both natural and synthetic sources. For the most preferred compound of the invention i.e. 3-(2,3-dimethyl-3-hydroxycyclopentyl)butanal, a convenient source of the olefinic starting material is the thermal cracking of linalool a natural product produced from rosewood oil. This thermally cracked product, known conventionally as plinol, is typically obtained in good yields by heating linalool to a temperature of about 525° C. in a tubular reaction zone.

As mentioned above, the compounds of the invention are of interest as aroma chemicals in particular for use in perfumes and perfumed products such as for example soaps, deodorants, detergents and aerosols.

The invention is illustrated further in the following Example. The NMR spectrum was obtained at 60 MHz in deuterochloroform solution; the absorptions quoted are in ppm relative to a tetramethylsilane standard.

EXAMPLE I

The hydroformylation catalyst used was a heterogeneous catalyst containing about 1.0% w rhodium formed by reacting silica with a pre-formed complex of $(C_2H_5O)_3SiCH_2CH_2P(C_6H_5)_2$ with $RhH(CO)-[P(C_6H_5)_3]_3$.

The starting material was a mixture of isomers of 2,3-dimethyl-1-(1-methyl-vinyl)cyclopent-3-ol (plinol) which was prepared by the thermal cracking of linalool at 525° C.

The plinol mixture (8.0 g), the hydroformylation catalyst (2.0 g), benzene (5 ml) and cyclohexane (40 ml) were mixed in a 100 ml stainless steel autoclave. The autoclave was then pressurized to 80 atm with a mixture of equal volumes of carbon monoxide and hydrogen. The autoclave contents were then stirred at 100° C. for 4.5 hours. After cooling to room temperature the reaction mixture was filtered and fractionally distilled. The required product 3-(2,3-dimethyl-3-hydroxycyclopentyl)butanal was obtained in a yield of 5.3 g, b.p. 100°–103° C. at 0.9 mm Hg. The NMR spectrum of the product showed the following characteristic absorptions:

= 0.77 ppm (doublet,  ⎫
= 0.80 ppm (doublet,  ⎬ 3H)
= 0.97 ppm (doublet, 3H)
= 1.30 ppm (singlet, 3H)
= 9.83 ppm (multiplet, 1H)

The product possesses a fragrant muguet (lily-of-the valley) odor.

EXAMPLE II

A perfume composition of the muguet-type was prepared according to the following recipe:

| 200 | parts by weight | Citronellol |
| 250 | parts by weight | Hydroxycitronellal |
| 100 | parts by weight | Linalool |
| 50 | parts by weight | Linalyl acetate |
| 50 | parts by weight | beta-Phenyl-ethanol |
| 50 | parts by weight | alpha-Ionone+ |
| 30 | parts by weight | Citronellyl acetate |
| 30 | parts by weight | Terpineol |
| 30 | parts by weight | 4-(Tricyclo 5.2.1.0$^{2,6}$decylic-8-ene)-butanol+ |
| 20 | parts by weight | Benzyl acetate |
| 20 | parts by weight | 2-Methyl-3-(p-tert . butylphenyl)-propanol |
| 20 | parts by weight | alpha-Pentyl-cinnamic aldehyde |
| 20 | parts by weight | Indole+ |
| 10 | parts by weight | Cinnamic alcohol |
| 10 | parts by weight | Acetaldehyde ethyl linalyl acetal+ |
| 10 | parts by weight | cis 3-Hexenyl acetate+ |
| 800 | parts by weight | |

+10% solution in diethylene glycol mono-ethyl ether.

This composition had an acceptable muguet-like odor. However the odor character was very much improved and rounded off by the addition of 200 parts by weight of 3-(2,3-dimethyl-3-hydroxycyclopentyl)-butanal.

What is claimed is:

1. A cyclopentane derivative according to the formula:

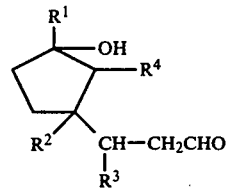

wherein $R^1$ and $R^4$ each represents an alkyl group of 1 to 4 carbon atoms; and $R^2$ and $R^3$ each represents a hydrogen atom or an alkyl group of 1 to 4 carbon atoms.

2. The cyclopentane derivative according to claim 1, wherein one of the groups $R^2$ and $R^3$ is alkyl and the other is hydrogen.

3. 3-(2,3-dimethyl-3-hydroxycyclopentyl)butanal.

* * * * *